United States Patent [19]

Eagle

[11] Patent Number: 5,744,106
[45] Date of Patent: Apr. 28, 1998

[54] HEATED SCENT DISPENSER

[76] Inventor: Richard E. Eagle, 2068 Carleton Rockwood Rd., Carleton, Mich. 48117

[21] Appl. No.: 730,152

[22] Filed: Oct. 15, 1996

[51] Int. Cl.$^6$ .............................. A61L 9/03; A01M 31/00
[52] U.S. Cl. ............................ 422/306; 43/1; 239/129; 239/136; 422/125
[58] Field of Search ...................... 422/306, 125, 422/5; D22/125; 239/136, 129; 43/1, 129

[56] References Cited

U.S. PATENT DOCUMENTS

| | | |
|---|---|---|
| 611,560 | 9/1898 | Chambers . |
| 4,771,563 | 9/1988 | Easley . |
| 4,937,431 | 6/1990 | Jameson et al. . |
| 5,060,411 | 10/1991 | Uhlman . |
| 5,094,025 | 3/1992 | Daniels . |
| 5,359,801 | 11/1994 | Mattucci et al. . |

*Primary Examiner*—Mary E. Mosher
*Attorney, Agent, or Firm*—Terrance L. Siemens

[57] ABSTRACT

An improved heated scent dispenser is provided. The device has a reservoir which is heated by igniting paraffin or an equivalent fuel. A wick draws fuel from a fuel tank containing the paraffin, the wick being enclosed in a first chamber to avoid exposure to the elements. A second chamber disposed above the first chamber contains a fluid reservoir which can be filled with animal urine or other scent. A dome top is disposed above the housing to distribute the scent horizontally in all directions. The entire assembly is contained within a shroud to provide additional protection from exposure to wind, rain, snow, etc. so as to be operable in virtually any environment. The device may also be used to distribute insect repellent or other similar aromatic by removing the heating tank and filling the fuel tank with the aromatic. Once ignited, the fumes are distributed out of open scent reservoir.

1 Claim, 2 Drawing Sheets

HEATED SCENT DISPENSER

BACKGROUND OF THE INVENTION

1. Field of the Invention

The present invention relates to scent dispensers and methods of making the same. More particularly, the invention contemplates an improved scent dispenser which has many different applications.

Thus it can be seen that the potential fields of use for this invention are myriad and the particular preferred embodiment described herein is in no way meant to limit the use of the invention to the particular field chosen for exposition of the details of the invention.

A comprehensive listing of all the possible fields to which this invention may be applied is limited only by the imagination and is therefore not provided herein. Some of the more obvious applications are mentioned herein in the interest of providing a full and complete disclosure of the unique properties of this previously unknown general purpose article of manufacture. It is to be understood from the outset that the scope of this invention is not limited to these fields or to the specific examples of potential uses presented hereinafter.

2. Description of the Prior Art

Scent dispensers are old and well known in the art. The following known prior art has been directed to providing a summary of the devices of the prior art. As will be seen, the simplicity and effectiveness of my invention is not rivaled in the prior art.

U.S. Pat. No. 5,359,801 discloses a scent dispenser which has a source of liquid fuel such as propane which is both expensive and highly explosive for heating a liquid scent such as animal urine. A reservoir containing the scent is heated by a centrally located exhaust pipe. The scent then rises out of the reservoir and is dispersed into the surrounding atmosphere. By contrast, the present invention has a reservoir for containing the scent but the scent is dispersed by a domed top in a radial pattern.

U.S. Pat. No. 4,937,431 issued to Jameson et al. discloses a scent distribution apparatus which uses an electronically controlled resistive heating device to heat a scent pad. By contrast, the present invention contemplates a scent distribution device which requires no batteries or electronics, and is reliable, durable and inexpensive to maintain.

U.S. Pat. No. 4,771,563 discloses a scent enhancement device which has an electrically heated reservoir for heating a small quantity of animal urine. By contrast, the device of the present invention uses paraffin or an equivalent fuel source for heating the animal urine.

U.S. Pat. No. 611,560 discloses a medicinal vaporizer which uses a candle for heating a medicinal aromatic. The candle is placed in an open chamber. By contrast, the device of the present invention uses paraffin or an equivalent fuel to heat a reservoir containing an animal scent. The fuel is drawn through a wick which is contained in a chamber for shielding the flame from wind and other elements such as rain and snow. Thus it can be used outdoors in virtually any conditions.

U.S. Pat. No. 5,094,025 discloses an animal scent heater which uses a battery powered resistive heating element to heat an animal scent. The scent rises vertically when heated. By contrast, the present invention uses a domed top to ensure that the scent is distributed horizontally in all directions once heated.

None of the above inventions and patents, taken either singly or in combination, is seen to describe the instant invention as claimed.

SUMMARY OF THE INVENTION

Briefly, the invention comprises an improved heated scent dispenser which has a reservoir which is heated by igniting paraffin or an equivalent fuel. A wick draws fuel from a fuel tank containing the paraffin, the wick being enclosed in a first chamber to avoid exposure to the elements. A second chamber disposed above the first chamber contains a fluid reservoir which can be filled with animal urine or other scent. A domed top is disposed above the second chamber to distribute the scent horizontally in all directions. The entire assembly is contained within an outer shell to provide additional protection from exposure to wind, rain, snow, etc. so as to be operable in virtually any environment. The device may also be used to distribute insect repellent or other similar aromatic by removing the heating tank and filling the fuel tank with the aromatic. Once ignited, the fumes are distributed out the top horizontally because of the dome top.

Accordingly, it is a principal object of the invention to provide new and improved heated scent dispenser which overcomes the disadvantages of the prior art in a simple but effective manner.

It is a major object of this invention to provide an improved heat scent dispenser which can be used under many different environmental conditions.

It is another object to provide a heated scent dispenser which has a dome top arrangement which causes the scent to radiate horizontally in all directions.

It is another object of the invention to provide a heated scent dispenser which requires no batteries and has no complicated electronic circuitry.

It is another object of the invention to provide a heated scent dispenser which has an outer shell to prevent burns and to further isolate the device from the environment.

It is another object of the invention to provide an improved heated scent dispenser which has many applications.

It is another object of the invention to provide an improved heated scent dispenser which can be used indoors as well as outdoors.

Finally, it is a general goal of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

The present invention meets or exceeds all the above objects and goals. Upon further study of the specification and appended claims, further objects and advantages of this invention will become apparent to those skilled in the art.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
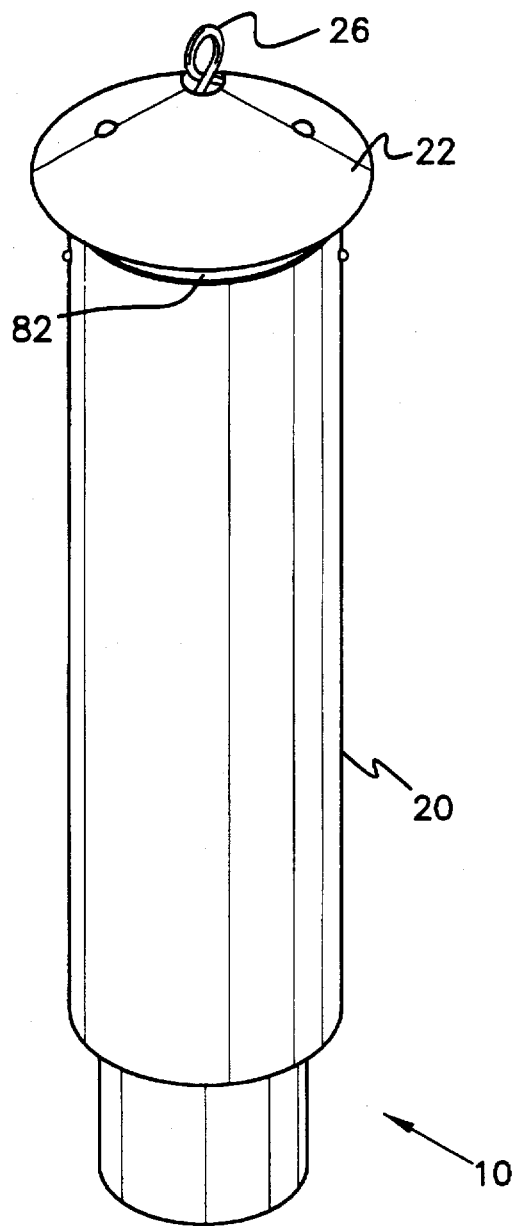
FIG. 1 shows a perspective view of the heated scent dispenser of the present invention.
Figure 2:
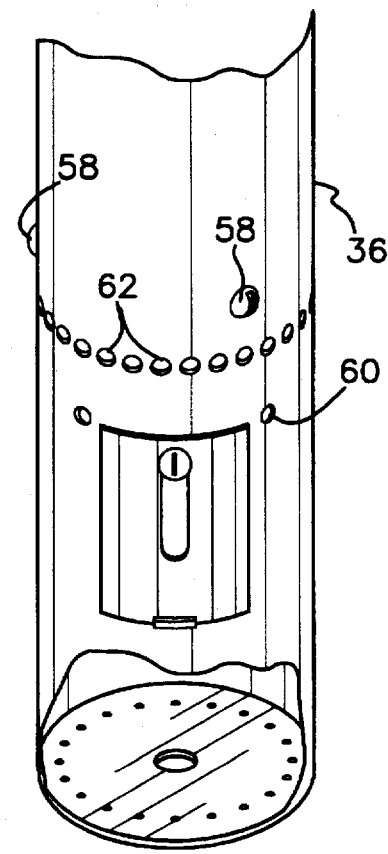
FIG. 2 is a partially broken away perspective view of the fluid reservoir and burner housing.
Figure 3:
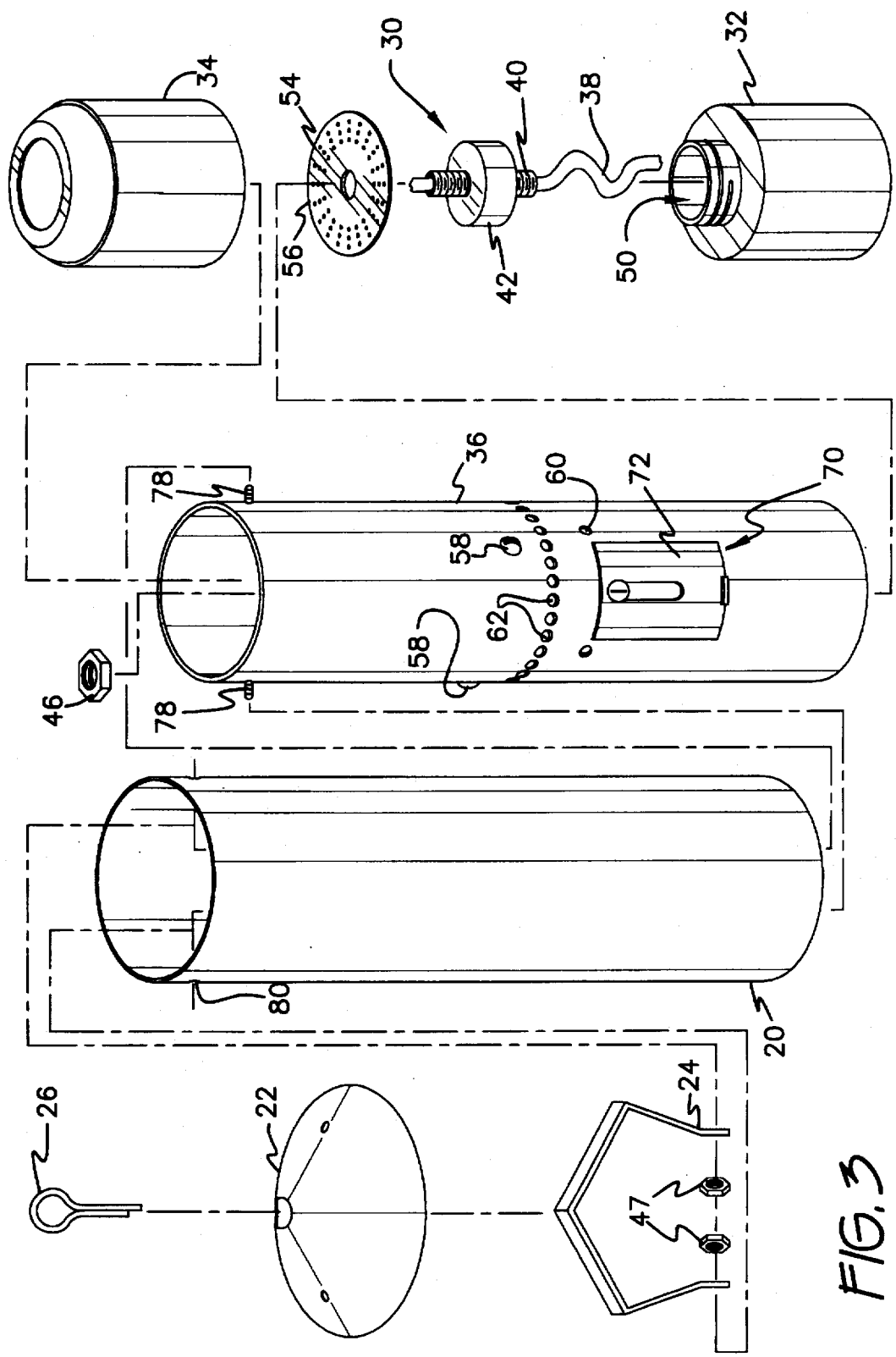
FIG. 3 shows an exploded perspective view of the heated scent dispenser of the present invention.

Referring now to FIGS. 1-3, a perspective view of the heated scent dispenser of the present invention, generally indicated by the numeral 10, is shown. The outer housing or shell 20 in combination with the top 22 enclose the entire apparatus and acts as a shield against wind, rain, and other environmental conditions. The shell 20 also has a relatively low surface temperature which allows for handling of the dispenser 10 and reduces the risk of burns. A cotter pin 26 protrudes from an aperture on the top 22 to allow the present invention 10 to be suspended from a support (not shown).

The top 22 is suspended above the shell 20 by a metal strap member 24 which allows for air to pass under the top 22 but minimizes the extent to which rain or snow can enter the outer housing. The top 22 is attached onto the metal strap 24 which is attached to the housing 36.

The fuel tank 32 is attached to the bottom of housing 36.

The burner assembly 30, and fluid reservoir 34 are contained within a housing 36. The burner assembly 30 includes a wick 38 which extends into and through a central bore which is formed in a threaded bolt 40. The bolt 40 extends through a threaded aperture in disc 42, the disc 42 acting as a cover for the fuel tank 32 as will be explained later. A nut 46 can be tightened to secure the wick 38, bolt 40, disc 42 and apertured baffle 54 to the housing 36.

The wick 38 may be inserted into the fuel tank with the lid 42 acting as a top or a cover to prevent spilling of the fuel.

Fluid reservoir 34 is contained within a cylindrical housing 36 which is placed above the fuel tank 32 and burner assembly 30. Space is provided within the cylindrical housing for the burner 30, and the fluid reservoir 34 is disposed directly above the burner. Fluid reservoir 34 rests on screws 58.

Inner housing 36 has apertures 60 and 62 to provide correct ventilation for the present invention 10.

Access to the wick 38 is provided by lighting hole 70, an aperture formed in housing 36. The lighting hole 70 is normally covered by sliding door 72 which is held in place within the housing 36 by a screw 80 which it slides up and down on. The sliding door 72 must be vertically lifted to reveal the lighting hole 70.

A pair of mutually opposed, screws with nuts 78 are provided at the top of the housing 36. The screws with nuts 78 attach bracket 24 to housing 36 and screws 78 extend through apertures 80 formed in shell 20 when they are aligned therewith.

In operation, the fluid reservoir 34 is filled with the desired liquid scent, and the fuel tank 32 is filled with fuel, preferably paraffin as has been previously discussed. The wick 38 may then be lighted via lighting hole 70 by moving the sliding door 72 to the appropriate position. The shell 20 may then be placed over the housing 36, with care being taken to ensure that the screws 78 extend through aperture 80 in the shell 20. Fumes from the heated scent will then pass out into the atmosphere via the gap 82 between the top 22 and the shell 20. If desired, the invention 10 may be used to disperse a flammable insect repellant such as citronella. This can be accomplished by filling the fuel tank 32 with the insect repellant and removing the fluid reservoir 34. The wick 38 may then be ignited.

It is to be understood that the provided illustrative examples are by no means exhaustive of the many possible uses for my invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

I claim:

1. A heated scent dispenser for heating aromatic liquids and solids comprising:

A vertically disposed inner housing having a top end, a bottom end and a substantially hollow interior for containing a fluid reservoir, a burner assembly, and a fuel tank attached to the bottom thereto;

said fuel tank being attached to said bottom end of said inner housing and being capable of containing a quantity of fuel;

said burner being disposed above and axially aligned with said fuel tank, the burner capable of igniting said fuel to supply heat to said reservoir;

a first baffle disposed below said burner to control air flow into said inner housing to insure constant flame;

the fluid reservoir being disposed above and axially aligned with said fuel tank and said burner;

a dome top to prevent ambient weather conditions from interfering with dispensing of said scent;

and an outer housing for containing said inner housing, said outer housing removably attached to said inner housing and spaced therefrom to allow said fumes to be exhausted from said scent dispenser.

* * * * *